United States Patent [19]

Varecka et al.

[11] Patent Number: 5,019,512

[45] Date of Patent: May 28, 1991

[54] SPIN FILTER FOR REMOVING SUBSTANTIALLY CELL-FREE CULTURE MEDIUM FROM SUSPENSION CELL CULTURE SYSTEM

[75] Inventors: Roland Varecka, Hayward; Rudolf F. Bliem, Castro Valley, both of Calif.

[73] Assignee: Baxter International Inc., Deerfield, Ill.

[21] Appl. No.: 325,286

[22] Filed: Mar. 17, 1989

[51] Int. Cl.[5] ........................ C12M 3/02; C12M 3/06
[52] U.S. Cl. .............................. 435/240.25; 435/286; 435/311; 435/312; 435/813; 435/284
[58] Field of Search ............... 435/284, 286, 311, 312, 435/313, 314, 315, 800, 813, 240.1, 240.2, 240.25; 436/177; 210/780, 784, 791, 383, 392, 396

[56] References Cited

U.S. PATENT DOCUMENTS

| | | | |
|---|---|---|---|
| 3,186,917 | 6/1965 | Gerhardt et al. | 195/1 |
| 4,535,062 | 8/1985 | Müller | 435/289 |
| 4,576,718 | 3/1986 | Reischl et al. | 210/616 |
| 4,586,779 | 6/1986 | Ono | 435/286 |
| 4,639,422 | 1/1987 | Geimer et al. | 435/286 |
| 4,649,118 | 3/1987 | Anderson | 435/316 |

FOREIGN PATENT DOCUMENTS

0086539 2/1983 European Pat. Off. .
0191356 8/1986 European Pat. Off. .
0317874 11/1988 European Pat. Off. .
60-259179 6/1984 Japan .
1296575 12/1984 U.S.S.R. .

OTHER PUBLICATIONS

Perry's Chemical Engineer's Handbook, 6th Edition, pp. 27-5-27-6.
Varecka, R. et al., "Use of a Rotating Wire Cage for Retention of Animal Cells in a Perfusion Fermentor", Develop. Biol. Standard., vol. 66, pp. 269-272 (1987).
"Continuous Cultures Without Wash-Out", Biotechnology, Nov. 1984.
Feder, Joseph et al., "Mass Culture of Mammalian Cells in Perfusion Systems", ABL, pp. 24-36, Jan.-Feb., 1985.
"ViTis-BioSpin Dynamic Filter", Product Literature.

Primary Examiner—David L. Lacey
Assistant Examiner—J. D. Waack
Attorney, Agent, or Firm—St. Onge Steward Johnston & Reens

[57] ABSTRACT

A spin filter for removing substantially cell-free medium from a stirred suspension culture vessel, wherein a stationary baffle is arranged in the interior space of the spin filter to disrupt liquid flow therein and minimize the tendency of cells to collect on and foul the inner-facing filter surfaces, the filter surface being sized to substantially exclude materials greater than about 8 to 10 microns, and the spin filter being rotatable independent of, and in a rotational direction opposite to, the vessel stirring device.

6 Claims, 3 Drawing Sheets

SPIN FILTER FOR REMOVING SUBSTANTIALLY CELL-FREE CULTURE MEDIUM FROM SUSPENSION CELL CULTURE SYSTEM

BACKGROUND OF THE INVENTION

The present invention relates to the in vitro culture of animal cells, and more particularly to a spin filter for removing substantially cell-free culture medium from a perfusion-type suspension cell culture system.

The in vitro culture of animal cells, particularly for purposes of recovering proteins either normally secreted by such cells or secreted by such cells by virtue of manipulation of their genetic machinery, has assumed increasingly greater prominence as a consequence of the increasing need for large quantities of proteins for therapeutic, diagnostic and investigative purposes, and the recognition that animal cells (per se, or as a hybrid partner, or as a host for an exogeneous gene) offer the best source of proteins which are the same as or closely similar to those actually employed by animals (e.g., humans) in vivo in carrying out regulatory, immune response, and other like functions.

Despite the recognized advantages of, and needs for, in vitro animal cell culture, the culture of cells outside the animal body is a difficult proposition at best, made even more difficult by the present-day demand that such processes be carried out efficiently and economically so as to achieve ultimate protein products which are not unreasonably expensive.

Among the known in vitro animal cell culture devices and systems exhibiting potential for mass production of cell-secreted proteins are the perfused fermenters, i.e., culture vessels in which animal cells are cultured in suspension in a culture medium which is agitated to promote homogeneity, and in which culture fluid is continuously or intermittently drawn off and replaced with a corresponding volume of fresh culture medium. Such suspension culture systems can be employed to culture anchorage-dependent cells by arranging such cells on suitable substrate materials (microcarrier particles), and are of course also useful for culture of cells which do not require attachment to surfaces in order to grow and proliferate.

Among the more significant problems related to perfused suspension culture systems is the difficulty of periodic or continuous removal of culture fluid from the vessel without at the same time removing cells suspended in the fluid. Numerous proposals and devices have been postulated and/or constructed to alleviate this problem, generally involving some means of filtration to separate cells from medium as medium is withdrawn from the vessel. One device which has achieved a degree of commercial acceptance is a so-called "spin filter", i.e., a rotating cage-like hollow cylinder immersed in the cell/medium suspension in the vessel and designed to exclude cells, but not liquid, from entering its interior space from which medium will be withdrawn from the system via an appropriate effluent overflow tube in association therewith. Typically, the spin filter comprises a core liquid-impermeable cylinder surrounded by a concentric liquid-permeable cylindrical mesh or screen, such that an annular cylindrical space exists between the outer surface of the core cylinder and the inner surface of the surrounding concentric cylindrical mesh to define the area from which cell-free medium can be withdrawn from the suspension culture vessel. The combined core and concentric screen rotate as a unit, either by independent rotation means or by being affixed to the shaft which drives the culture vessel impeller for agitating the suspension of cells and medium.

In the development of filters for attaining cell separation before withdrawal of medium, considerable attention has been devoted to the appropriate sizing of the pores or apertures in filtering surface. Clearly one way to insure that medium but not cells pass through the filter into the interior annular region for removal from the vessel is to utilize filter materials having aperture sizes smaller than the cell size. For cells grown on microcarriers or for cells which grow as aggregates in suspension, such criterion generally permits relatively large apertures which are less prone to clogging or fouling and which are readily permeable to the culture fluid. However, for cells (e.g., hybridomas) which grow as single cells in suspensions, extremely small apertures are needed in order to exclude cells on the basis of size alone. Depending upon the particular aperture size, perfusion rate and cell density, use of such small filter apertures will lead to extensive clogging and fouling of the filter surfaces within a very short time, e.g., within about one week for systems involving aperture sizes of less than about ten (10) microns, cell densities of greater than about $10^6$ cells/ml. and perfusion rates of greater than about 0.5 volumes of medium perfused per reactor volume per day. As a compromise solution, the aperture size is generally chosen to be larger than the cell size and as a consequence, complete retention of cells in the culture vessel as medium is withdrawn is not possible. Moreover, even operation in this manner does not completely eliminate fouling and clogging which limits the useful life of the spin filter and requires that the culturation be ceased to regenerate or replace the filter.

SUMMARY OF THE INVENTION

The primary object of the present invention is to provide a spin filter for the suspension culture of cells, particularly of cells which generally grow as single cells in suspension.

Another object of the invention is the provision of a spin filter which enables the withdrawal of substantially cell-free medium from the suspension culture vessel while at the same time being less susceptible to clogging and fouling such that it can remain in operation for extended periods of time at reasonably high cell densities and perfusion rates, thereby enabling suspension culture of cells to the high densities required for commercial-scale production of cell-secreted proteins.

These and other objects as will be apparent are provided by an impeller-driven suspension culture apparatus for the in vitro perfusion suspension culture of animal cells suspended in a liquid culture medium, the apparatus comprising a culture vessel; within the vessel, an impeller rotatable in a given direction to promote the axial flow of cells and medium within the vessel; an inlet for addition to the vessel of culture medium; within the vessel, a spin filter which is rotatable independent of the vessel impeller and in a rotational direction opposite thereto, the spin filter comprising a vertically-oriented hollow receptacle made of porous liquid-permeable material, such that at least a portion of the interior of the hollow receptacle defines a substantially cell-free liquid withdrawal space for receiving culture medium from the culture vessel which has passed into the space across the porous liquid-permeable material of the receptacle;

liquid withdrawal means arranged in the liquid withdrawal space for withdrawing medium from the space and from the culture vessel; and one or more vertically-oriented baffles arranged in the liquid withdrawal space. The average pore size of the porous liquid-permeable material making up the surfaces of the hollow receptacle is such that it is sufficient to substantially exclude materials greater than about 8 to 10 microns in size, and in operation the spin filter is at least periodically, and preferably continuously, rotated in a rotational direction opposite to that of the vessel impeller.

In the preferred embodiments of the invention, the spin filter comprises a vertically-oriented liquid-impermeable core which is surrounded by, yet axially spaced from, the hollow receptacle so that the liquid withdrawal space is defined by the area between the core and the receptacle, and the baffles are arranged in that so-defined space. In the most preferred embodiment, the spin filter is cylindrical, i.e., having a cylindrical liquid-impermeable core, a surrounding hollow cylinder of the porous liquid-permeable material concentric thereabout, and a liquid withdrawal space which is defined by the annular area between the concentric core and hollow cylinder.

The present invention is predicated upon investigation of the phenomena associated with the fouling and clogging of the filter surfaces of spin filters, and discovery of effects which produce fouling and clogging. In particular, it has been found that fouling of the filter by cells generally occurs by reason of cells passing through the filter pores and then accumulating on the inner-facing filter surfaces. In typical spin filter operation, the liquid in the liquid withdrawal space rotates at the same speed as the filter itself and, as a consequence, there is no surface sweeping effect to prevent cells from accumulating on the inner-facing filter surface (via natural attachment and/or centrifugal force). At the same time, another contributor to fouling is protein debris, which preferentially tends to associate with the outer-facing filter surfaces.

As a consequence of the foregoing observations and studies, the spin filter of the present invention takes into account features and modes of operation designed to counteract the normal fouling effects. Thus, the pore or aperture size of the liquid-permeable material of the filter is chosen to be small so as to reduce the tendency for cells to pass through the apertures and collect on the inner-facing filter surfaces. In addition, to deal with those cells which do pass through the filter into the liquid withdrawal space, one or more stationary vertically-oriented baffles is arranged in the liquid withdrawal space (e.g., associated with the liquid overflow tube therein and/or suspended in the space from separate means emanating, e.g., from a cover plate over the vessel) to break down liquid motion in the liquid withdrawal space and thus substantially prevent cells from collecting on the inner-facing filter surfaces. The baffle or baffles are referred to as stationary baffles in the sense that they are independent of the spin filter surfaces per se, i.e., they do not rotate with the spin filter as it rotates. Finally, for minimizing the tendency of protein debris to collect on the outer-facing filter surfaces, the spin filter is adapted to rotate in a direction opposite that of the impeller which agitates the vessel contents.

By virtue of the construction and operation of the spin filter according to the present invention, cell retention rates of greater than 90% have been attained in single cell suspension culture systems with useful filter operating life (i.e., before fouling) of over 3 weeks, at cell densities of about $8 \times 10^6$ to $2 \times 10^7$ cells/ml. and volumetric perfusion rates of 1 to 5.5 liters per liter reactor per day.

The invention is further described with reference to the drawings and the detailed description provided hereinafter.

DETAILED DESCRIPTION OF THE INVENTION

Figure 1:
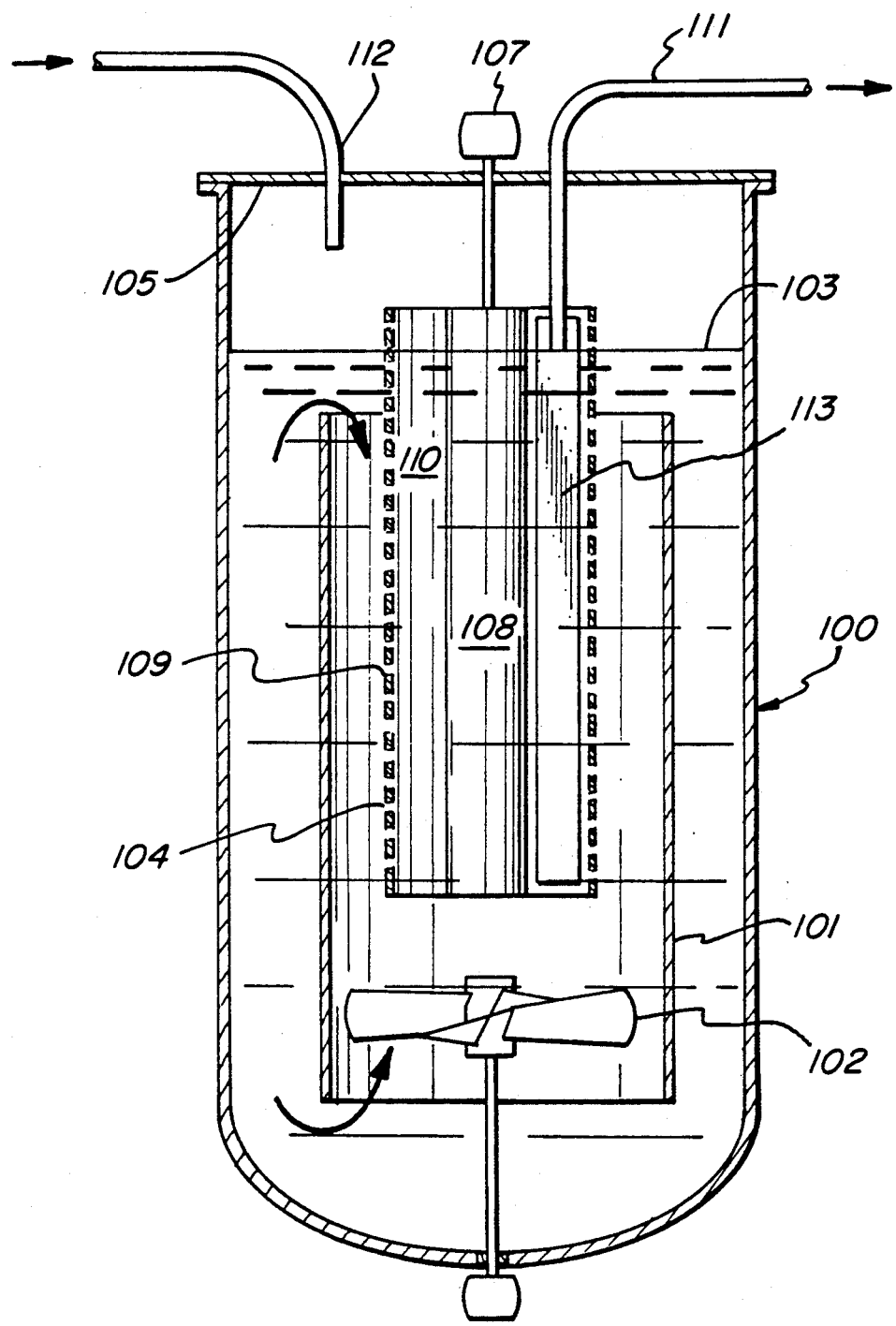
FIG. 1 is a sectional view of a suspension culture vessel employing a spin filter in accordance with the invention.

In the preferred embodiment of the invention, and with reference to FIG. 1, there is shown a suspension culture vessel 100, generally constructed of biologically compatible sterilizable material such as glass, but most preferably stainless steel. Within the culture vessel is a draught tube 101 and a motor-drive impeller 102 which generally directs flow vertically upward through the draught tube for overflow at its top region, establishing an overall axial mixing of cells and the medium in which they are suspended and preventing cell-sedimentation. The general operating liquid level in the vessel is shown as 103.

Arranged within the culture vessel 100 is a spin filter, generally designated as 104, which is suspended in the liquid suspension from a top cover plate 105 over the vessel, and which is affixed to rotation drive means 107 which are independent of the drive means for impeller 102 and which are capable of rotating the spin filter 104 in a rotational direction opposite that of the impeller 102.

The spin filter 104 consists of an inner core cylinder 108 which is liquid-impermeable. The core cylinder 108 may be solid or hollow and, if the latter, is closed at its top and bottom, and is preferably constructed of stainless steel or other like material. Surrounding core cylinder 108 is a concentric hollow cylindrical shell 109 having a larger cross-sectional diameter than that of the core cylinder such that an annular cylindrical space 110 exists therebetween. The hollow cylindrical shell 109 is composed of porous liquid-permeable material, preferably a stainless steel mesh, having apertures of from about 5 to 10 microns so as at least nominally capable of excluding solid particles having diameters larger than about 10 microns. The core cylinder 108 and concentric hollow cylinder 109 are affixed in any suitable manner (e.g., at their bases) for rotation in tandem, so long as the annular space 110 remain open at the top. As shown, the annular space 110 at the bottom of the spin filter is completely closed, although it is possible to have the closure be by way of the mesh materials, i.e., such that liquid can pass therethrough. The important consideration is that any liquid in annular space 110 have arrived there by passing across the porous liquid-permeable material from which hollow cylindrical shell 109 is made.

Arranged in the upper region of the annular space 110 is a liquid level tube 111 through which substantially cell-free culture medium in annular space 110 will rise and exit from the culture vessel in response to an increase in liquid level such as brought about by feed of fresh or replenished culture medium through feed port 112.

Arranged in the annular space 110, preferably substantially throughout its vertical length, is a stationary baffle or vortex breaker 113. For ease of construction, baffle 113 can be associated with level tube 111, but it is also possible to suspend the baffle independently from cover plate 105 or in any other suitable way which maintains its generally stationary character relative to the rotation of the spin filter device. Although one baffle is shown in the FIG. 1, multiple baffles may be employed.

In continuous or semi-continuous perfusion operation, a volume of culture medium is fed into the culture vessel via inlet tube 112. The contents of the vessel are axially stirred by rotation of impeller 102, and spin filter 104 will be rotated in the opposite direction. Cell-containing medium in contact with filter shell 109 will pass substantially cell-free into annular space 110 by reason of the small pore size of the filter material, and is withdrawn from the annular space as the liquid level 103 in the vessel rises above the bottom of level tube 111. The stationary baffle 113 serves to disrupt liquid flow in the rotating annular space 110 so as to minimize the tendency of any cells which have passed through filter 109 to collect on the inner-facing filter surfaces. At the same time, the rotation of the spin filter opposite to that of impeller 102 reduces the tendency of protein debris to collect on and foul the outer-facing filter surfaces.

As a consequence of the invention, it is possible to employ filter pore or aperture sizes which inherently insure that a large majority of the cells in suspension will be excluded from the annular space thereby substantially increasing the ability to remove essentially cell-free medium from the culture vessel. At the same time, however, the pronounced tendency of such small filter pores to clog and foul is substantially minimized by virtue of the baffle arrangement and the counterrotation of the spin filter.

Figure 2:
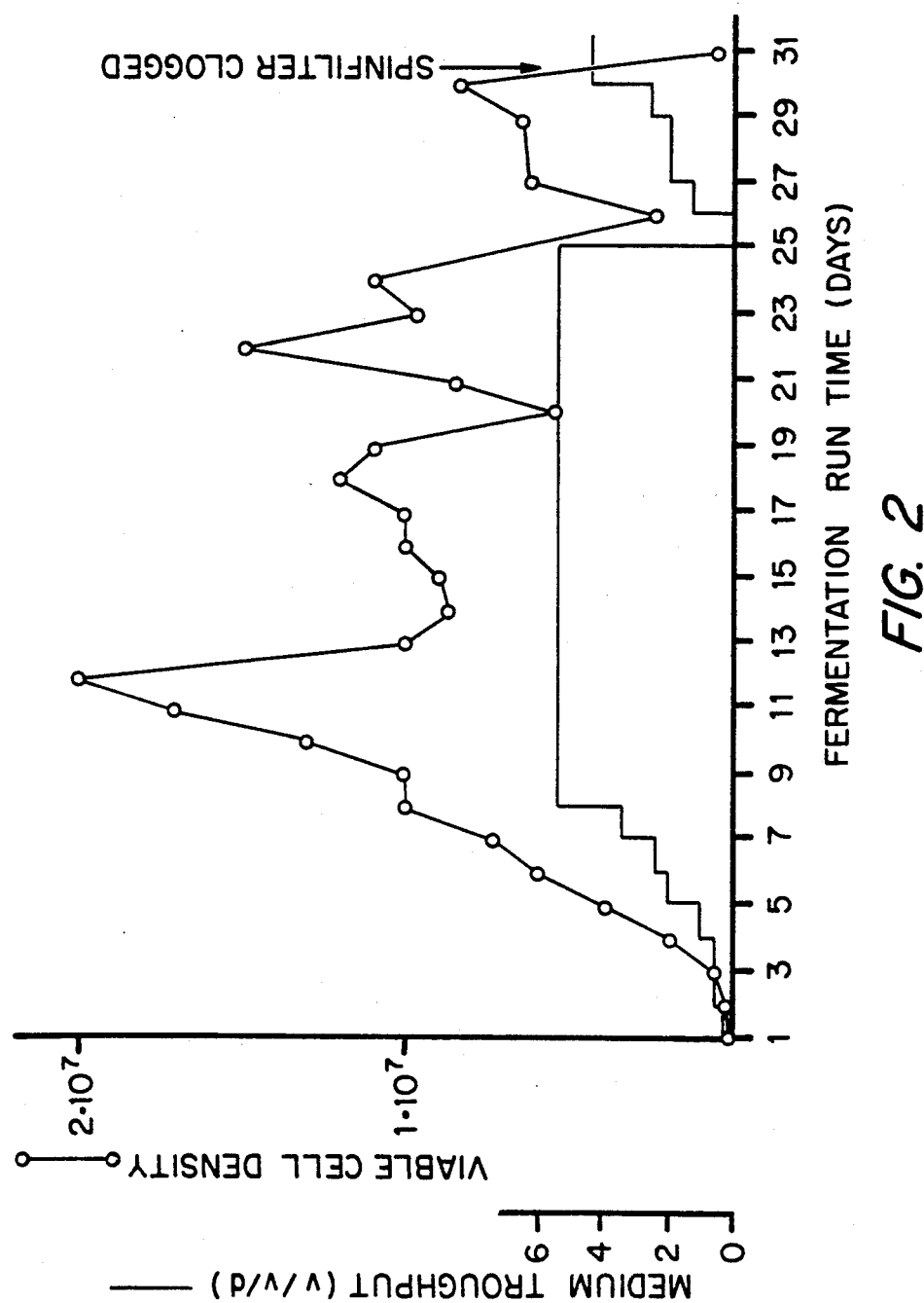
FIGS. 2 and 3 represent graphs of data collected in a comparison of the spin filter system according to the invention and a commercially-available spin filter system.
Figure 3:
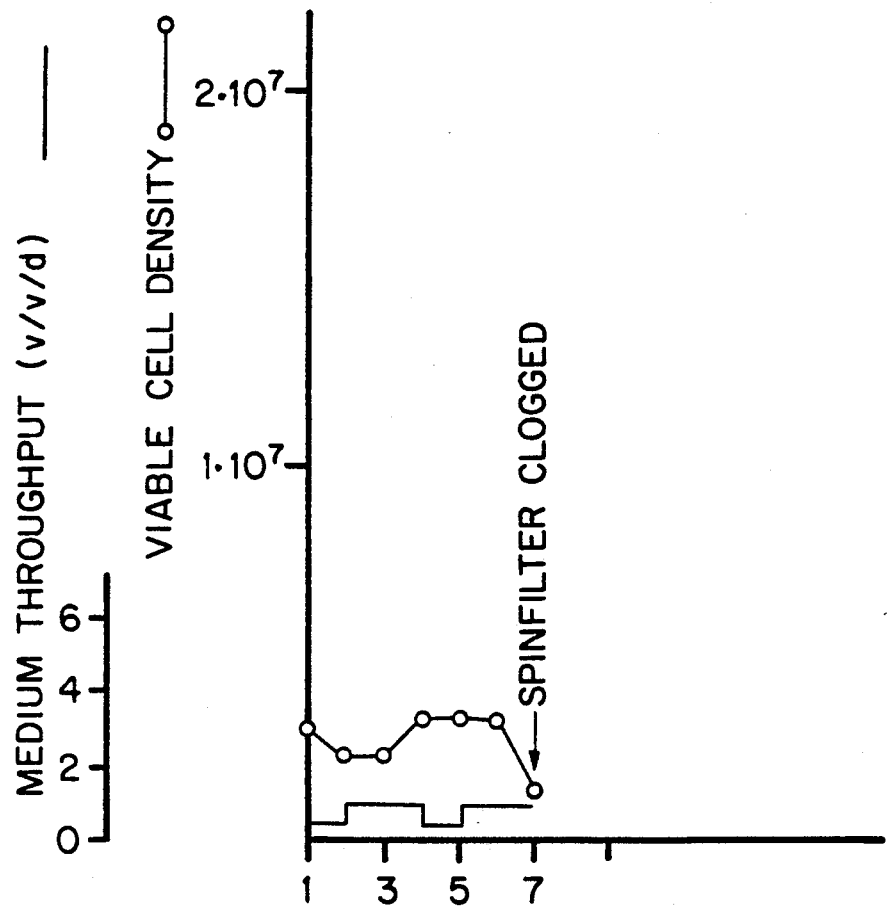

The advantages of the present invention can be seen in the graphically-presented data of FIGS. 2 and 3. In these tests, otherwise identical suspension culture perfusion vessels were operated side-by-side in culture of cells which grow as single cells in suspension. In the control reactor (data shown in FIG. 3), the spin filter (cylindrical screen surrounding solid core) had an 8 micron pore size and was rotated at the same rate and in the same direction as the vessel impeller. In the reactor according to the invention (data shown in FIG. 2), the spin filter was identical in all respects except for the presence of a vertical baffle suspended from the vessel cover into the annular space between the spin filter core and surrounding cylindrical screen, and the rotation of the spin filter, while at the same rate as in the control, was in a direction opposite that of the vessel impeller.

In the system according to the invention, the perfusion rate was gradually increased over time to as high as 5.5 liters of medium/liters of reactor/day, leading to attainment of high viable cell densities, i.e., operating the system at commercially-desirable conditions yet most susceptible to filter clogging. In contrast, perfusion rates for the control reactor were maintained at relatively low levels of about 0.5 liters/liters/day and consequent low viable cell densities, i.e., conditions designed not to challenge the spin filter capabilities too drastically. Nevertheless, within one week the spin filter in the control reactor clogged, while that in the system according to the invention operated about thirty (30) days without significant clogging even under the conditions of high perfusion rate/high cell density.

Although the invention has been described with reference to particular preferred features and exemplary parameters, these are intended to illustrate rather than limit the scope of the invention, as defined in the appended claims.

What is claimed is:

1. A suspension culture apparatus for the in vitro perfusion suspension culture of animal cells suspended in liquid culture medium therefor, comprising:
   a culture vessel;
   an impeller within said culture vessel;
   first rotating means for rotating said impeller in a given axial direction in a plane substantially perpendicular to the longitudinal axis of said vessel for promoting axial flow, relative to said longitudinal axis, of cells and culture medium within said culture vessel;
   an inlet in liquid communication with said culture vessel for at least intermittent addition of culture medium to said culture vessel;
   a spin filter arranged in said culture vessel, and oriented substantially along said longitudinal axis, comprised of a hollow receptacle composed of porous liquid-permeable material, at least a portion of the interior of said hollow receptacle defining a substantially cell-free liquid withdrawal space for receiving culture medium from said culture vessel which has passed into said withdrawal space across said porous liquid-permeable material of said receptacle, said porous liquid-permeable material having an average pore size sufficient to substantially exclude passage therethrough of materials greater than about 8 to 10 microns in size;
   second rotating means, distinct from said first rotating means, for at least periodically rotating said spin filter independent of, and in an axial direction, relative to said longitudinal axis, opposite to that of, said impeller;
   liquid withdrawal means arranged in said liquid withdrawal space for at least intermittently removing substantially cell-free culture medium from said space and from said culture vessel; and
   one or more vertically-oriented stationary baffles arranged in said liquid withdrawal space.

2. The apparatus according to claim 1 wherein said spin filter further comprises a vertically-oriented liquid-impermeable core which is surrounded by, and radially spaced apart from, said hollow receptacle, and wherein said liquid withdrawal space is defined by the area between said core and said hollow receptacle.

3. The apparatus according to claim 2 wherein said core and said hollow receptacle are cylindrical, and wherein said liquid withdrawal space is defined by the annular area between said cylindrical core and said cylindrical hollow receptacle.

4. The apparatus according to claim 3 further comprising a cover over said culture vessel, and wherein said spin filter and said baffle are suspended in said culture vessel from said cover.

5. The apparatus according to claim 4 wherein said liquid withdrawal means are suspended from said cover, and wherein at least one said baffle is affixed to said liquid withdrawal means.

6. A method for the in vitro perfusion suspension culture of animal cells in culture medium, comprising:

(a) providing a suspension cell culture apparatus comprised of:
  a culture vessel;
  an impeller within said culture vessel;
  first rotating means for rotating said impeller in a given axial direction in a plane substantially perpendicular to the longitudinal axis of said vessel for promoting axial flow, relative to said longitudinal axis, of cells and culture medium within said culture vessel;
  an inlet inn liquid communication with said culture vessel for at least intermittent addition of culture medium to said culture vessel;
  a spin filter arranged in said culture vessel, and oriented substantially along said longitudinal axis, comprised of a hollow receptacle composed of porous liquid-permeable material, at least a portion of the interior of said hollow receptacle defining a substantially cell-free liquid withdrawal space for receiving culture medium from said culture vessel which has passed into said withdrawal space across said porous liquid-permeable material of said receptacle, said porous liquid-permeable material having an average pore size sufficient to substantially exclude passage therethrough of materials greater than about 8 to 10 microns in size;
  second rotating means, distinct from said first rotating means, for at least periodically rotating said spin filter independent of, and in an axial direction, relative to said longitudinal axis, opposite to that of, said impeller;
  liquid withdrawal means arranged in said liquid withdrawal space for at least intermittently removing substantially cell-free culture medium from said space and from said culture vessel; and
  one or more vertically-oriented stationary baffles arranged in said liquid withdrawal space.
(b) providing said culture vessel with an inoculum of animal cells and with culture medium therefor;
(c) agitating the contents of said culture vessel by rotation of said impeller by said first rotating means;
(d) at least periodically introducing culture medium into said culture vessel through said inlet in liquid communication with said culture vessel, and at least periodically withdrawing substantially cell-free culture medium from said liquid withdrawal space through said liquid withdrawal means; and
(e) at least periodically rotating said spin filter, by said second rotating means, in an axial direction opposite to the axial direction of said impeller.

* * * * *